United States Patent
Lentrichia et al.

(10) Patent No.: US 7,198,902 B2
(45) Date of Patent: Apr. 3, 2007

(54) APPARATUS AND METHOD FOR SEPARATING VIRAL PARTICLES FROM CELLS

(75) Inventors: Brian B. Lentrichia, Acton, MA (US); Steven A. Hecht, Cambridge, MA (US)

(73) Assignee: Cytyc Corporation, Marlborough, MA (US)

( * ) Notice: Subject to any disclaimer, the term of this patent is extended or adjusted under 35 U.S.C. 154(b) by 286 days.

(21) Appl. No.: 10/671,929

(22) Filed: Sep. 25, 2003

(65) Prior Publication Data

US 2005/0069867 A1   Mar. 31, 2005

(51) Int. Cl.
*C12Q 1/68* (2006.01)

(52) U.S. Cl. ............................. 435/6; 435/7.1
(58) Field of Classification Search ............ 435/6, 435/7.1; 210/90
See application file for complete search history.

(56) References Cited

U.S. PATENT DOCUMENTS

| | | |
|---|---|---|
| 4,849,332 A | 7/1989 | Lorincz |
| 5,143,627 A | 9/1992 | Lapidus et al. |
| 5,364,597 A | 11/1994 | Polk, Jr. et al. |
| 5,705,627 A | 1/1998 | Manos et al. |
| 5,942,700 A * | 8/1999 | Radcliffe et al. ........ 73/863.24 |
| 6,318,190 B1 | 11/2001 | Radcliffe et al. |
| 6,905,594 B2 * | 6/2005 | Ferguson ..................... 210/90 |

OTHER PUBLICATIONS

Lakewood Pathology Associates, P.A. "Women's Health: Cervical Cancer", 1998, Web site page http://www.lakewoodpath.com/health/WH/wh-specimen.html, 2 pages.
Zymed Laboratories, Inc., MaxArray HPV Control Cell Block, 2 pages, Feb. 12, 2003.
Lucanus Gynaecology -HPV, "Recommendations for the Diagnosis and Treatment of HPV Infections of the Female Tract"; Web site page http://www.lucanus.co.nz/HPV.htm, 8 pages, Feb. 12, 2003.
DIGENE Laboratory Information, "Hybrid Capture Technology" Web site page http://www.digene.com/lab_4.html, 3 pages, Feb. 12, 2003.

* cited by examiner

*Primary Examiner*—Ali R. Salimi
(74) *Attorney, Agent, or Firm*—Theodore Allen; Mark Casey

(57) ABSTRACT

A method for analyzing a sample to detect cells infected by Human Papilloma Virus (HPV) is provided. The method includes passing a medium containing the sample across a filter. The filter has a pore size that is greater than a dimension of a HPV particle, but smaller than a dimension of a HPV infected cell, such that most of the HPV particles pass through the filter, while leaving the cells on the filter. The material collected on the filter is then examined to determine if HPV infected cells are present in the material.

5 Claims, 4 Drawing Sheets

APPARATUS AND METHOD FOR SEPARATING VIRAL PARTICLES FROM CELLS

FIELD OF THE INVENTION

The invention pertains to devices and methods for collecting and detecting a biological material, and more particularly, to devices and methods for separating biological material from viral particles.

BACKGROUND

Human Papilloma Virus (HPV) belongs to the Papovaviridae family, which includes double-stranded members of Papilloma viruses and polyoma viruses. HPV infects the epithelial surfaces of skin or mucosa, causing a warty growth known as condyloma. More than 100 types of HPV have been identified. In addition to benign warty growths, HPV may also be associated with several types of neoplasms.

Cells infected with HPV may undergo changes in cellular morphology, typified by an apparent clearing of the cytoplasm surrounding the nucleus of the HPV infected cell. Such cellular morphology associated with the HPV infected cells may be observed microscopically and used for diagnosis of HPV. Koilocytosis is the term used to describe the cytopathic effect induced by HPV infection. The observed presence of koilocytes in a cytological preparation of exfoliated epithelial cells from the cervix provides one criterion for categorizing a cytologic diagnosis of Low Grade Squamous Intraepithelial Lesion (LGSIL) according to the Bethesda Classification System. Patients classified with a diagnosis of LGSIL, a pre-neoplastic condition, are generally referred to a gynecologic oncologist for colposcopy.

As with many pathologic viruses, it is believed that HPV inside cells (intracellular HPV) is associated with the development of pre-neoplastic disease, while HPV outside the cells (extracellular HPV) is more closely associated with the normal condition of the cells. Therefore, in a diagnostic procedure, it would be desirable to prepare a sample such that it contains no or a fewer number of extracellular HPV, and to base a diagnostic result on such prepared sample. Thus, the determination of HPV cells will correlate more closely with a diagnosis of LGSIL than with a diagnosis of "Within Normal Limits" (WNL).

Various methods have been employed for detection of HPV. For example, liquid-based assay methods typically involve collection of exfoliated epithelial cells and the surrounding extra cellular milieu, and placing the sample into a medium, such as a detergent. The medium dissolves the sample, which is then analyzed to detect HPV. Because the medium employed in such method typically destroys the morphological integrity of the cells, the dissolved solution is homogeneous in that it does not allow intracellular HPV to be distinguished from extracellular HPV.

A pap smear test, which has application in the detection of early cancer of the uterine cervix, may be used to detect HPV. To perform a pap smear test, a physician collects cells by brushing and/or scraping a skin or mucous membrane in a target area with an instrument. The cells are then smeared onto a glass slide, and are fixed and transported to a laboratory where the slide is stained. The glass slide is then examined under a microscope by a cytotechnologist and/or a pathologist to identify cellular abnormalities. During evaluation, a pathologist may employ a polychrome technique, characterized by staining the nuclear part of the cells, to determine the presence of dysplasia or neoplasia. The pathologist may also apply a counter-stain for viewing the cytoplasm of the cells. Because the sample of the pap smear test may contain debris, blood, mucus, and other obscuring artifacts, the pap smear test may be difficult to evaluate, and may not provide an accurate diagnostic assessment of the collected sample.

Cytology based on the collection of the exfoliated cervical cells into a liquid preservative offers many advantages over the traditional method of smearing the cells directly onto the slide. A slide can be prepared from the cell suspension using a filter transfer technique, as disclosed in U.S. Pat. Nos. 6,572,824, 6,318,190, and 5,772,818, which are expressly incorporated herein by reference. Debris, blood and mucus is greatly reduced by the combined method of liquid collection and filtering to transfer the cells onto a glass slide.

Intracellular HPV can be detected by a slide-based assay known as in-situ hybridization. In this method, a sample is first collected. The sample is then denatured, hybridized, washed, and stained according to appropriate probe specifications. After the sample is appropriately prepared, it is then examined on a slide to detect HPV. Although the in-situ hybridization can be used to detect and verify intracellular HPV, it is often difficult and laborious to perform, and the result may be open to subjective interpretation.

An alternative method for detecting HPV involves the use of the Hybrid Capture® System, marketed by Digene Corporation, located in Gaithersburg, Md. The Hybrid Capture® System is a signal amplification assay utilizing antibody capture and chemiluminescent signal detection. Such an assay requires clinical specimens to be combined with an alkaline solution, which disrupts the virus and releases the target DNA. The target DNA then combines with specific RNA probes to create RNA:DNA hybrids, which are then captured onto a solid phase coated with capture antibodies specific for the RNA:DNA hybrids. The captured RNA:DNA hybrids are then detected with antibodies conjugated to alkaline phosphatase. Because the Hybrid Capture® method does not distinguish released DNA originated in extracellular HPV from released DNA originated in intracellular HPV, such method also does not allow intracellular HPV to be distinguished from extracellular HPV.

SUMMARY OF THE INVENTION

According to a first aspect of the invention, a method for analyzing a sample to detect cells infected by HPV is provided. The method includes passing a medium containing the sample across a filter. By way of non-limiting examples, the medium may be poured onto the filter, or alternatively, a pneumatic force or pressure may be used to draw the medium across the filter. In another method, the filter may be moved through the medium. The method may also include preparing the material collected on the filter for examination. The filter has a pore size greater than a dimension of a HPV particle but smaller than a dimension of a HPV infected cell. For example, the pore size can range from 0.2 microns to 10 microns.

Next, the material collected on the filter is examined to determine if HPV infected cells are present in the material. Various methods may be used to prepare the collected material for examination. By way of non-limiting examples, the materials collected on the filter may be prepared and examined by placing the collected material onto a slide for viewing under a microscope, or by using a Hybrid Capture® method as described herein. In one embodiment, the material may be placed on the slide by applying a pneumatic force across the filter. Other conventional methods known in the art may also be used to examine the collected materials.

According to another aspect of the invention, a method for separating cells from extracellular HPV is provided. The method comprises passing a medium containing the cells and extracellular HPV particles across a filter to collect a majority of the cells on the filter, while passing a majority of the extracellular HPV particles through the filter. The filter may have the same pore characteristics described above, and the medium can be filtered in the same manner as that described above.

According to still another aspect of the invention, a method for separating cells from extracellular HPV is provided. The method comprises passing a medium across the filter to collect a substance, which has an extracellular HPV to cell ratio that is substantially less than the extracellular HPV to cell ratio of the medium. The filter may have the same pore characteristics described above, and the medium can be filtered in the same manner as that described above.

In its broadest aspects, the invention is not limited to separating cells from extracellular HPV particles. The previously described methods can be used to separate biological material from viral particles.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DESCRIPTION OF THE PREFERRED EMBODIMENTS

Figure 1:
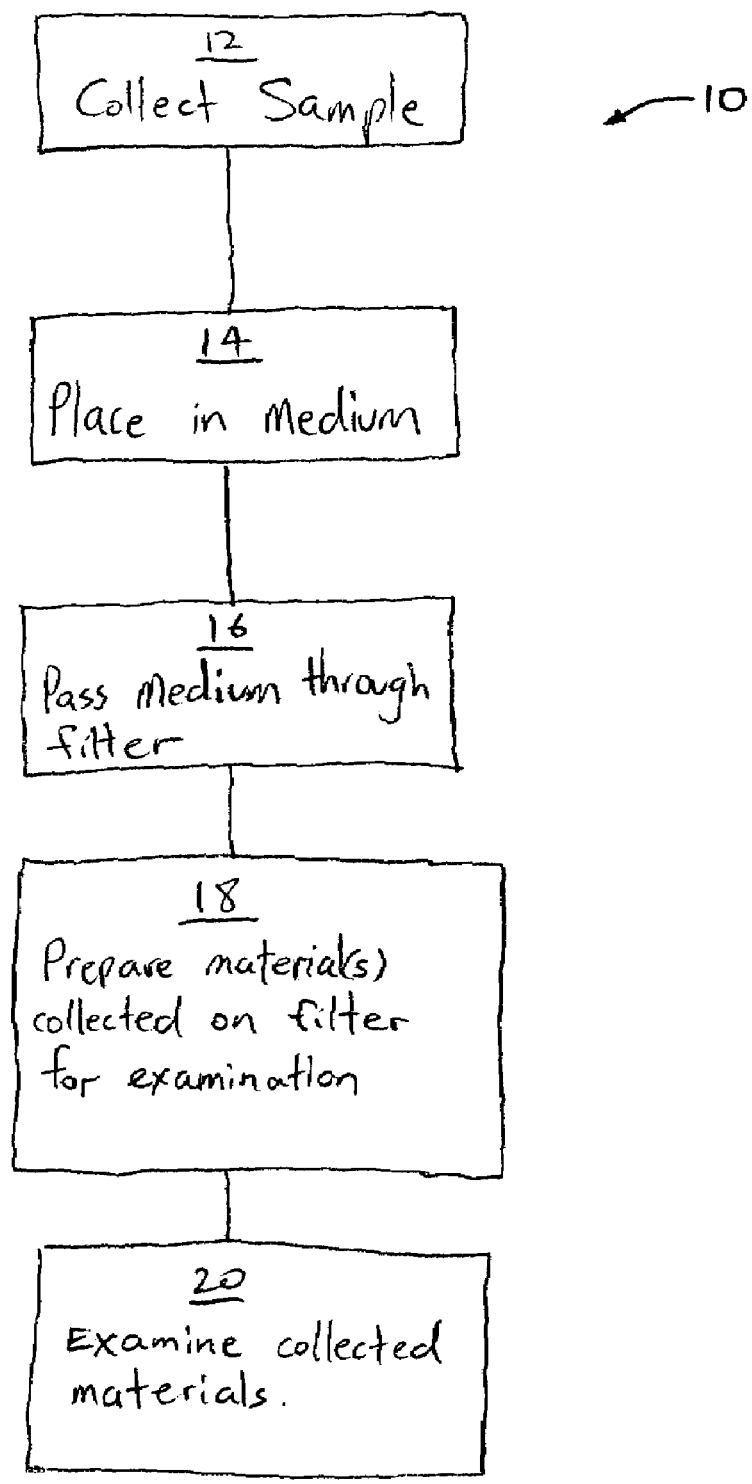
FIG. 1 is a flow diagram illustrating a method for analyzing a sample in accordance with the invention.

Referring to FIG. 1, a method 10 for determining whether a patient is infected with intracellular HPV will now be described. Initially, a sample is collected from the patient for diagnosis of a HPV condition (Step 12). The sample may be collected from any area of the patient where HPV can be found, such as the cervix, vulva, vagina, urethra, bladder, perianal skin, rectum, and penis. Various devices may be used to collect the sample. In one sample collection process, a cervical sample may be harvested by a two-stage technique, which includes sampling of the endocervical canal with a cytobrush, as well as obtaining a sample from the transformation zone with a medical spatula. In another cervical sample collection process, either the cytobrush or the spatula alone may be used. In yet another cervical sample collection process, Cervex Brush®, available at Unimar, Inc., or Accellon Combi®, available at Medscand, both of which combine the action of the cytobrush and spatula, may be used to collect the sample. Other methods known in the art for collecting a sample may also be used, and the scope of the invention is not limited to a particular collection apparatus or method.

Once a sample is collected, it is placed in a container containing a selected medium (Step 14). In one sample preservation process, the medium includes a digestive enzyme, such as, e.g., collagenase and elastase. The digestive enzyme acts as a dissolving fluid that disintegrates the structure of the sample, but does not affect the structural integrity of the individual cells within the sample. Other known chemicals capable of performing such functions may also be used. Alternatively, the sample may be disintegrated using a tool designed or adapted for such purpose, and then placed in a selected medium. In this case, the medium may or may not comprise a digestive enzyme. In another sample preservation process, the collected sample may be placed in a preservative fluid for subsequent use.

Next, the medium, which contains the disintegrated sample, is passed through a membrane or filter having a plurality of pores (Step 16). The pores of the filter are sized such that they prevent cells, such as cells infected with HPV, from passing through, while allowing most or all of the extracellular HPV particles to pass through. For example, a filter having an 8 micron nominal pore size is employed in one embodiment. Since HPV particles have a dimension of about 50 nanometers, extracellular HPV particles will pass through the filter if they are present in the sample. In contrast, epithelial cells have a cross sectional dimension that are generally greater than 8 microns. Therefore, if HPV infected cells are present in the sample, they will be retained on the filter without passing through it. In alternative embodiments, a filter having a pore size that is within the range of 0.2 micron to 12 microns may also be used.

The minimum number of HPV genomes, each viral particle containing one genome, that is required to provide a positive result for the Hybrid Capture 2 assay is about 11,400. This number can be calculated from 0.05 pg of HPV DNA that is used in each Hybrid Capture assay to determine positive or negative specimen result in the assay and the fact that the HPV genome has 8000 base pairs. Therefore, if fewer than 11,400 HPV particles remain with the cells after filtration, the specimen is considered negative for HPV by the Hybrid Capture 2 method. Cells that have been cultured from cervical cancer specimens range from 2 HPV genomes per cell (the SiHa cell line) to 600 genomes per cell (CaSki cell line). A positive specimen by Hybrid Capture 2 would require 600 SiHa cells but only 2 CaSki cells.

As a result, material collected on the filter will have an extracellular HPV to cell ratio (i.e., the number of extracellular HPV particles over the number of cells) that is substantially reduced from the extracellular HPV to cell ratio of the unfiltered sample. The correlation between a diagnosis of intracellular HPV and an actual occurrence of intracellular HPV will be increased by examining the collected material rather than the unfiltered sample.

The filter may be made from a variety of materials such as polycarbonate. For example, polycarbonate membrane marketed by the Nuclepore Corporation in Pleasanton, Calif., may be used. Other filters can be formed from materials including cellulose, nylon, polyester, Teflon®, or any other suitable material. Further details regarding the construction and use of such filters are disclosed in U.S. Pat. Nos. 5,364,597 and 5,942,700, the entire disclosures of which are expressly incorporated by reference herein.

Figure 2A:
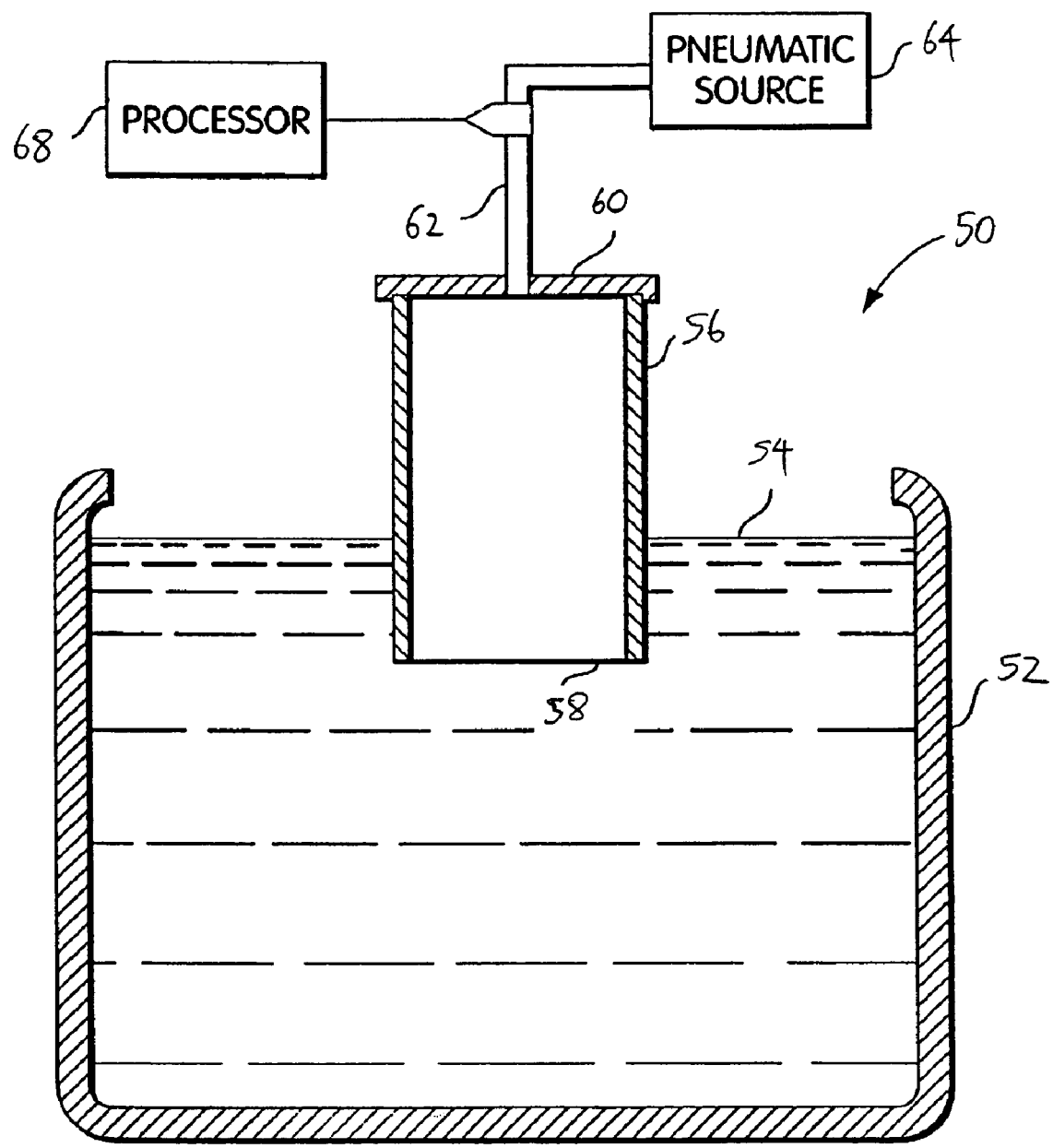
FIG. 2A is a side view of a preferred embodiment of a system that can be used in the method of FIG. 1 to separate cells from extracellular HPV particles.

Various methods may be used to pass the medium through the filter. In one method, filtering may be accomplished by a filter transfer method. FIG. 2A illustrates a system 50 that may be used to perform a filter transfer method. The system 50 includes a container 52, a fluid suspension of dispersed particles 54, a particle collection device 56, a filter 58, a cap 60, a conduit 62, a pneumatic source 64, and a processor 68. The container 52 holds the fluid sample 54 and makes it available for sampling by the collection device 56. The collection device 56 may be a filter cylinder device manufactured and marketed by the Cytyc Corporation of Boxboro, Mass. In the illustrated embodiment, the fluid sample 54 is the medium that contains the collected sample, and the filter 58 is the filter, as described previously with reference to step 16 of the method 10.

In one filtering process, the system 50 rapidly rotates the particle collection device 56 to actuate the fluid sample 54 and disintegrate clumps of particles that may exist within the fluid sample 54. For example, with a fluid sample 54 having contained therein a population of epithelial cells, the actuation of the collection device 56 can disintegrate clumped cells, such that there exists within the fluid sample 54 a population of individual cells, and a reduced population of clumped cells. Alternatively, if the clumped cells are already disintegrated, i.e., by a dissolving medium, as discussed previously, then this step may not be necessary.

Figure 2B:
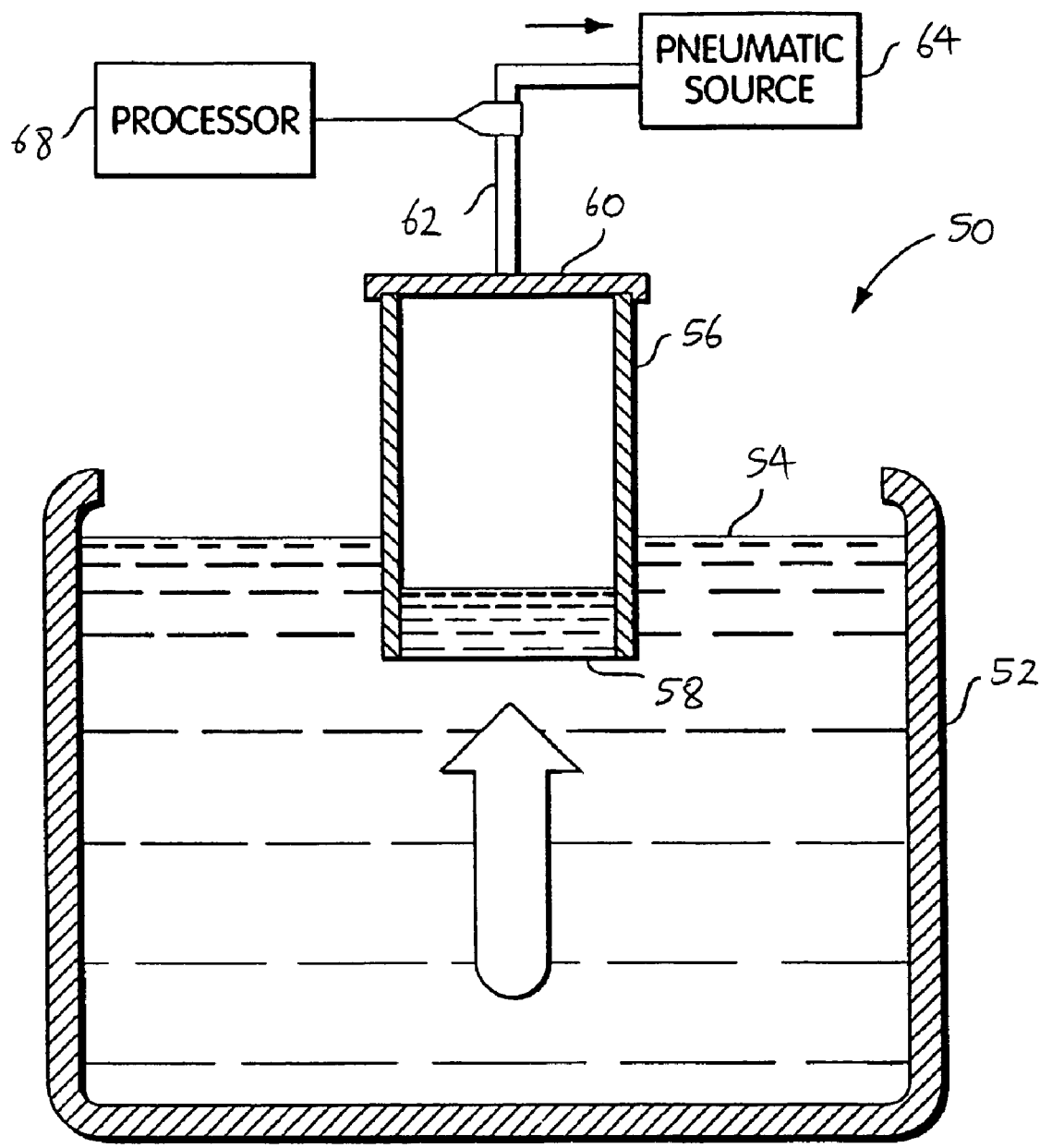
FIG. 2B is a side view of the system of FIG. 2A, particularly shown in operation for separating the cells from the extracellular HPV particles.

The system 50 uses a pneumatic particle collection technique, wherein pneumatic action is provided by the pneumatic source 64 to draw a portion of the fluid sample 54 past the filter 58 and into the collection device 56. FIG. 2B depicts the system 50 having drawn a portion of the sample fluid 54 across the filter 58 and into the interior of the collection device 56. The pneumatic source 64 creates a negative pressure within the interior of the collection device 56, which generates a flow of the fluid sample 54 across the filter 58. Drawing a fluid sample 54 across the filter 58 causes cells dispersed within the fluid sample 54 to collect against the filter 58 and, in particular, to block the pores of the filter membrane. Viral particles, such as extracellular HPV particles, if they are present in the fluid 54, will either pass through the pores of the filter 58 as the fluid 54 is drawn across the filter 58, or remain in the fluid 54.

During filtering of the sample, the processor 68 determines a measure representative of the quantity of cells that have collected against the filter 58. The action of blocking the pores of the filter membrane 58 is understood to effectively decrease the porosity of the filter membrane 58. That is, as cells collect against the filter surface 58, the pores of the filter 58 are sealed, thereby reducing the number of pores available for passing fluid to the interior of the collection device 56. The amount of time it takes for the negative pressure to return to equilibrium after the pneumatic source has changed the interior pressure within the collection device 56 is dependent, in part, on the number of pores of filter 58 available for passing fluid into the interior of the collection device 56. The reduction of available pores increases the amount of time it takes for the vacuum inside the collection device 56 to return to equilibrium. Further, the rate of pressure change within the collection device 56 changes as pores are blocked. Accordingly, the pressure change and rate of pressure change within the collection device 56 is representative of the number of cells that have collected against the surface of the filter 58. The processor 68 can track the pressure within the collection device 56 and determine, responsive thereto, a number representative of a quantity of cells collected against the filter 58. Therefore, upon extraction of the collection device 56 from the sample 54, the system 50 has collected a substantially known quantity of cells from the fluid sample 54. Such filter transfer methods are described in U.S. Pat. No. 5,942,700, which was previously mentioned herein.

Figure 3:
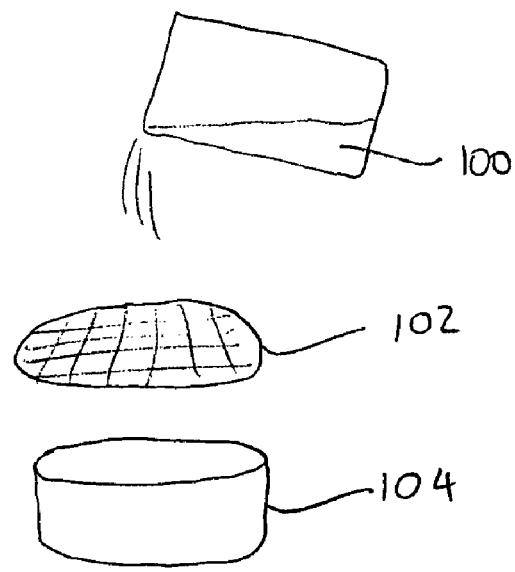
FIG. 3 is a perspective view of another preferred embodiment of a system that can be used in the method of FIG. 1 to separate cells from extracellular HPV particles.

In another filtering process, as shown in FIG. 3, the medium containing the sample (i.e., medium 100) is simply poured over a filter 102. The filter 102 is described previously with reference to step 16. Most or all of the extracellular HPV, if present, will pass through the pores of the filter 102 together with the medium 100, while cells are retained by the filter 102, as discussed previously. A separate container 104 may be used to contain the medium 100 that has passed through the filter 102.

Figure 4:
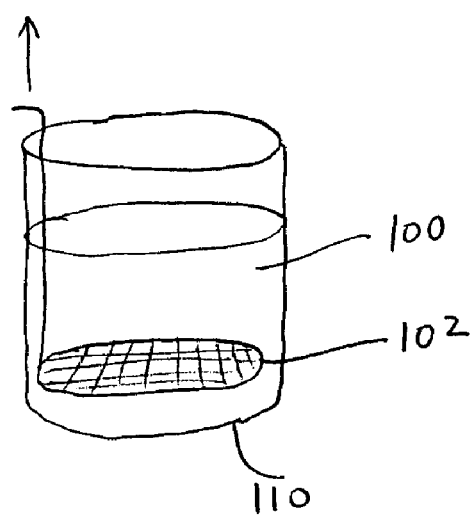
FIG. 4 is a perspective view of yet another preferred embodiment of a system that can be used in the method of FIG. 1 to separate cells from extracellular HPV particles.

In yet another filtering process, the filter 102 is moved over the medium 100. For example, the filter 102 may be placed at a bottom of a container 110, and the medium 100 containing the dissolved or disintegrated sample is then poured into the container 110 (FIG. 4). Alternatively, instead of disintegrating the sample first, the sample may be placed over the filter 102 in the container 110, and the medium 100, which contains a digestive enzyme, is then poured into the container 110 to dissolve the sample. Next, the filter 102 is moved through the medium 100, collecting HPV infected cells that may be present in the medium 100, while leaving most or all of the extracellular HPV in the medium 100.

Optionally, the sample may be further filtered by one or more additional filters, which may have a larger or smaller pore size than the first filter 102. For example, further filtering using a filter that has larger pore size may be beneficial in that it allows any artifacts that are larger than HPV infected cells to be separated from the HPV infected cells, which may or may not be present in the collected sample. In this case, materials collected on the first filter may be placed in another medium, which is then caused to pass through the additional filter. Any of the above described filtering techniques may be used to perform such further filtering.

It should be noted that a prerequisite of viral internalization into the cell is binding of the viral particle to the cell surface. Cell surface targets for a variety of pathogenic organisms have been identified. An example is cell-surface hyaluronic acid as a receptor target for Chlamydia trachomatis. The specific cell-surface target for HPV has not been identified specifically, however it may be an epithelial cell specific target since other cells types (i.e. neural, endothelial, stromal) have not been characterized to contain HPV. HPV bound to the epithelial cell surface, but not yet internalized by the cell, may affect the results of the filtration method described herein as long as more than about 11,400 HPV particles remain adhered to the cells. In Situ hybridization studies have not revealed HPV particles bound to the exterior of the cell, however the process of In Situ hybridization is rigorous and involves treating the cell specimen with enzyme, many reagents, temperature changes and washing steps that may scour the surface of the cells of any bound virus particles.

Returning to FIG. 1, after the material is collected on the filter, the material is prepared for subsequent examination (Step 18). If the originally collected sample contains intracellular HPV and extracellular HPV, the HPV infected cells will have been collected and separated from the extracellular HPV. Various techniques known in the art may be used to prepare the materials collected on the filter for examination. In one sample preparation process, a slide is prepared from the materials collected on the filter for subsequent examination using a conventional technique.

Alternatively, a ThinPrep® slide may be prepared by placing a uniform single layer of the collected material onto a glass slide. This can be accomplished by placing the outer surface of the filter on which the materials are collected onto a slide. Then a pneumatic pressure is applied across the filter to dislodge the collected materials from the outer surface of the filter and urge the dislodged material against the slide. The final product will essentially contain a monolayer of cells free of debris, blood, mucus, and other obscuring artifacts. Alternatively, the materials collected on the filter may be transferred to another container, which can then be used to prepare a ThinPrep® slide, as similarly discussed previously. Systems and methods for preparing ThinPrep® slides are described in U.S. Pat. Nos. 5,143,627 and 5,364,597.

After the sample preparation process has been completed, the prepared sample is then examined to determine if intracellular HPV is present (step 20). For example, the collected materials may be examined under a microscope, which may be automated such as that embodied in the ThinPrep Imaging System, marketed by Cytyc Corporation.

Other methods known in the art for examining cells may also be used. For example, the collected material may be examined to detect intracellular HPV using the Hybrid Capture® method described previously. In this case, instead of making a slide, the collected material is deposited into a vial containing a volume of cell lysing solution, such as an alkaline solution, which disrupts the virus and releases the target DNA. The target DNA then combines with specific RNA probes to create RNA:DNA hybrids, which are then captured onto a solid phase coated with capture antibodies specific for the RNA:DNA hybrids. The captured RNA:DNA hybrids are then detected with antibodies conjugated to alkaline phosphatase. The bound alkaline phosphatase is detected with a chemiluminescent dioxetane substrate. Upon cleavage by the alkaline phosphatase, the substrate produces light that is measured on a luminometer in Relative Light Units (RLUs). If the originally collected sample contains intracellular HPV, the output of the luminometer will indicate so. An example of an assay that utilizes antibody capture and chemiluminescent signal detection is the HC2 HPV Assay, available at Digene Corporation, located in Gaithersburg, Md.

Although several embodiments of the method have been described with reference to separating HPV infected cells from extracellular HPV, the method may also be used to separate different materials in a sample in different applications. For example, the method may be used in other clinical or laboratory applications, where it may desirable to collect or detect a biological material from a sample. In one method, the filtering process described in step 16 may be used to separate cells from extracellular viral particles other than HPV, such as Adenovirus or Epstein Barr Virus. Furthermore, the method may also be used to separate a biological material, such as a component of a cell, from a viral particle. The method may also be used to separate cell types by their size.

Thus, although different embodiments have been shown and described, it would be apparent to those skilled in the art that many changes and modifications may be made thereunto without the departing from the scope of the invention, which is defined by the following claims and their equivalents.

What is claimed is:

1. A method for analyzing a biological sample to detect the presence or absence of cells infected by human papilloma virus (HPV), comprising the steps of:
    obtaining a sample from a patient that may comprise cells infected by HPV;
    placing said sample in a liquid medium;
    passing said medium containing said sample across a filter to collect cells from said medium on said filter, said filter having a pore size that is greater than a dimension of a HPV particle but smaller than a dimension of a HPV infected cell; and
    examining said collected cells to determine if HPV infected cells are present.

2. The method of claim 1, wherein said pore size is within a range of 0.2 micron to 10 microns.

3. The method of claim 1, wherein said pore size is approximately 8 microns.

4. The method of claim 1, wherein said cells are epithelial cells.

5. The method of claim 1, wherein said cells are cervical cells.

* * * * *